(12) United States Patent
Selis

(10) Patent No.: US 8,075,569 B2
(45) Date of Patent: Dec. 13, 2011

(54) BIOPSY DEVICES AND METHODS

(76) Inventor: James E. Selis, Birmingham, MI (US)

( * ) Notice: Subject to any disclaimer, the term of this patent is extended or adjusted under 35 U.S.C. 154(b) by 0 days.

(21) Appl. No.: 12/702,730

(22) Filed: Feb. 9, 2010

(65) Prior Publication Data

US 2010/0145363 A1    Jun. 10, 2010
US 2010/0292711 A2    Nov. 18, 2010

Related U.S. Application Data

(62) Division of application No. 11/150,666, filed on Jun. 10, 2005.

(60) Provisional application No. 60/579,112, filed on Jun. 11, 2004.

(51) Int. Cl.
*A61B 17/10* (2006.01)
(52) U.S. Cl. .................................................. 606/139
(58) Field of Classification Search .......... 606/108, 606/139–142, 151, 157, 158, 198, 200, 213; 623/23.72, 23.74; 128/831, 843; 600/426
See application file for complete search history.

(56) References Cited

U.S. PATENT DOCUMENTS

| | | | |
|---|---|---|---|
| 5,441,487 A | 8/1995 | Vedder | |
| 5,526,822 A | 6/1996 | Burbank et al. | |
| 5,649,547 A | 7/1997 | Ritchart et al. | |
| 5,743,883 A | 4/1998 | Visconti | |
| 5,785,693 A | 7/1998 | Haining | |
| 5,853,366 A | 12/1998 | Dowlatshahi | |
| 5,893,856 A | 4/1999 | Jacob et al. | |
| 5,941,890 A | 8/1999 | Voegele et al. | |
| 6,056,700 A | 5/2000 | Burney et al. | |
| 6,063,062 A | 5/2000 | Paradis | |
| 6,113,611 A | 9/2000 | Allen et al. | |
| 6,161,034 A | 12/2000 | Burbank | |
| 6,181,960 B1 | 1/2001 | Jensen et al. | |
| 6,220,248 B1 | 4/2001 | Voegele et al. | |
| 6,228,055 B1 | 5/2001 | Foerster et al. | |
| 6,234,177 B1 | 5/2001 | Barsch | |
| 6,261,243 B1 | 7/2001 | Burney et al. | |
| 6,261,302 B1 | 7/2001 | Voegele et al. | |
| 6,347,241 B2 | 2/2002 | Burbank et al. | |
| 6,356,782 B1 | 3/2002 | Sirimanne et al. | |
| 6,371,904 B1 | 4/2002 | Sirimanne et al. | |
| 6,425,903 B1 | 7/2002 | Voegele | |
| 6,549,800 B1 | 4/2003 | Atalar et al. | |
| 6,575,991 B1 | 6/2003 | Chesbrough et al. | |
| 6,605,047 B2 | 8/2003 | Zarins et al. | |
| 6,656,192 B2 | 12/2003 | Espositio et al. | |
| 6,662,041 B2 | 12/2003 | Burbank et al. | |
| 6,723,108 B1 | 4/2004 | Jones et al. | |
| 6,766,186 B1 | 7/2004 | Hoyns et al. | |

(Continued)

FOREIGN PATENT DOCUMENTS

WO    9608208    3/1996

(Continued)

*Primary Examiner* — Melanie Tyson
(74) *Attorney, Agent, or Firm* — Dobrusin & Thennisch PC

(57) ABSTRACT

An improved system for mammography analysis and methods of using the same. In one aspect, the present invention provides a biopsy instrument having a side opening that generally coexists or is aligned with a central portion of a cyst, tissue or otherwise for deploying a marking device to the central region of the same. In another aspect, the present invention provides an encasement, adapted to receive a marking clip, for deployment into a tissue region for marking and/or treatment of the same.

20 Claims, 3 Drawing Sheets

U.S. PATENT DOCUMENTS

| | | |
|---|---|---|
| 2001/0034528 A1 | 10/2001 | Foerster et al. |
| 2002/0038087 A1* | 3/2002 | Burbank et al. .............. 600/431 |
| 2002/0165561 A1 | 11/2002 | Ainsworth et al. |
| 2003/0033006 A1* | 2/2003 | Phillips et al. ................ 623/1.36 |
| 2003/0050571 A1 | 3/2003 | Zarins et al. |
| 2004/0044364 A1* | 3/2004 | DeVries et al. ............... 606/213 |
| 2004/0049126 A1 | 3/2004 | Zarins et al. |
| 2004/0097981 A1 | 5/2004 | Selis |
| 2004/0236213 A1 | 11/2004 | Jones et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0119562 A1 | 6/2005 | Jones et al. |
| 2008/0294039 A1 | 11/2008 | Jones et al. |
| 2009/0030309 A1 | 1/2009 | Jones et al. |

FOREIGN PATENT DOCUMENTS

| | | |
|---|---|---|
| WO | 00/07506 A2 | 2/2000 |
| WO | 0024320 A1 | 4/2000 |
| WO | 0067833 A1 | 11/2000 |
| WO | 2007/060576 A2 | 5/2007 |

* cited by examiner

BIOPSY DEVICES AND METHODS

CLAIM OF BENEFIT OF FILING DATE

The present application is a divisional application of U.S. application Ser. No. 11/150,666, filed Jun. 10, 2005, which claims the benefit of the priority of U.S. Provisional Application Ser. No. 60/579,112 with a filing date of Jun. 11, 2004, all of which are incorporated herein by reference for all purposes.

CLAIM OF PRIORITY

The present application claims priority to U.S. Provisional Patent Application Ser. No. 60/579,112 (filed Jun. 11, 2004), the contents of which are hereby incorporated by reference in their entirety.

RELATED APPLICATION

The present application relates to the subject matter of, and expressly incorporates by reference, the teachings of commonly owned and invented U.S. Provisional Patent Application Ser. No. 60/547,844 (filed Feb. 26, 2004), U.S. patent application Ser. No. 10/631,204 (filed Jul. 31, 2003) and PCT/US2003/023995 (filed 31 Jul. 2003).

TECHNICAL FIELD

The present invention relates to devices and methods for performing biopsies, and more particularly to implantation of breast implantation clips for use as markers in mammography using a cyst aspiration needle. The present invention also relates to marking clips having an encasement for assisting in the deployment of the clip, the treatment of tissue surrounding the clip or otherwise as described.

BACKGROUND OF THE INVENTION

Percutaneous biopsy of the breast is a well-accepted alternative to open surgical biopsy with needle localization for those lesions seen by mammography or ultrasound but not able to be felt by the surgeon. When percutaneous biopsy is performed, it is frequently necessary to place a metal clip at the site of biopsy. This is done for several reasons. For example, the lesion biopsied might be partially or entirely removed. If the lesion is proven to be malignant, it is necessary to subsequently do a wide excisional biopsy after needle localization to remove any residual malignancy. The clip makes the site of biopsy apparent, assuring accurate localization. In addition, if something is seen on both mammography and ultrasound, it is not always certain that the lesions are one and the same. A biopsy under ultrasound guidance with placement of a clip allows confirmation by mammography that the lesion is the same or different than the one seen on the mammogram. Further, the presence of a clip seen on a mammogram alerts the radiologist that a biopsy has been performed, prompting the radiologist to more closely evaluate the site of biopsy.

The vast majority of percutaneous breast biopsies are performed under art-disclosed stereotactic guidance techniques, and generally use a device known as the Mammotome® (by Johnson & Johnson). The clip that is employed is generally prone to pinching a minute amount of breast tissue. Sometimes, the clip may fail to hold onto the tissue or the clip may migrate to a different undesired location.

U.S. Surgical has produced a clip from a wire with a memory that is delivered into the breast and forms a ring. It is larger in diameter than the Mammotome® device clip and can grab significantly more tissue. The clip is an alloy containing nickel. Recent indications are that U.S. Surgical may no longer manufacture this clip, thus creating a potential supply issue for existing users.

SenoRx, Inc. produces metal markers embedded in Gelfoam pellets (a product that promotes clotting of blood), called Gel Mark™. The product is packaged to include a plurality of pellets and one radiographic marker. The pellets, however, potentially result in undesired migration of particles.

Although there is current production of a hand-held Mammotome® device, for the purpose of ultrasound guided biopsy, for some users this device may be awkward and cumbersome to use. The majority of ultrasound-guided biopsies are done with use of Tru-cut needles. This can be done through a coaxial needle. A Bard 12 gauge biopsy needle could be used through an 11 gauge coaxial needle. Through this 11 gauge coaxial needle, a U.S. Surgical clip might also be delivered, although U.S. Surgical is not believed to have marketed their clip for use during ultrasound-guided biopsies.

Another product is manufactured by Inrad. This clip is used for placement during ultrasound-guided biopsy because the delivery device is steel and does not provide the flexibility necessary for delivery through the Mammotome® needle. This delivery device has a beveled tip, allowing advancement through breast tissue without a coaxial needle.

Breast biopsies using an 11 gauge coaxial needle have been performed. However, most biopsies are typically done using smaller needles, e.g. a 14 gauge biopsy needle with 13.5 gauge coaxial needle. Such small sizes, in many environments, however, are believed to be too small to efficiently allow advancement of the delivery device of current commercially available clips.

Turning to another consideration, when a cyst in the breast is aspirated, a spectrum of different types of fluid can be recovered. These might range in color from white to yellow to green or brown. They may be mucousy or bloody and thus can be thick or thin. Some physicians send all samples for cytology analysis, while other physicians may send only grossly suspicious samples (e.g. mucousy or bloody). Regardless of which cyst fluids are sent for cytology, once a cyst is evacuated or in the event that a cyst cannot be fully evacuated because it contains a solid component, a radiologist would like to place a clip into the lesion. It is often important to mark the cyst so that should the cytology prove malignant, or otherwise require further attention, the exact site of the lesion would be known and a needle localization could be subsequently performed.

In one particular aspect, with reference to FIGS. 1a and 1b, common prior biopsy instruments generally employ a clip delivery device 1 with a side tube opening 2 having a center "C" disposed within a needle 3. Typically the devices are constructed so that the user needs to longitudinally re-position the instrument (e.g., on the order of about 5 mm to 12 mm or more) between steps of removal of tissue, aspiration of a cyst, or both and marking of a biopsy site "A" with a clip 4, in order to locate the clip precisely in the biopsy site. This is because the distance "d" from the forward end of a leading portion 5 of the clip delivery device is less than the distance "D" to a center portion "$C_A$" of a biopsy site. For example, FIG. 1a illustrates an instrument with clip delivery device having a side tube opening for providing a side hole clip delivery function, but showing the result if there is no longitudinal re-positioning of the clip delivery device or the needle. As seen, upon deployment, the clip is not located precisely at the "$C_A$" biopsy site "A". As seen for example in FIG. 1b, in order to achieve precise location of the clip at the biopsy site "A", it is necessary either to shift the entire needle longitudinally, or to retract the clip delivery device longitudinally, the former being shown in the drawing. Either way, another manual step is required of the user. It is desirous to avoid this need for longitudinal re-positioning, while still achieving precise placement of a clip at the biopsy site.

There is a need for improved devices for breast biopsy, cyst aspiration or both, to overcome the above-discussed disadvantages of current commercial products.

The following United States patents are also useful to more fully understand the context and application of the present invention and are all hereby expressly incorporated by reference herein: U.S. Pat. No. 6,161,034; U.S. Pat. No. 5,526,822; and U.S. Pat. No. 5,649,547. Devices disclosed in the above patents may be modified as desired to incorporate the inventive features disclosed herein.

SUMMARY OF THE INVENTION

The present invention meets the above needs and contemplates providing a biopsy instrument for use in a manner that does not require longitudinal re-positioning of the instrument within a patient between steps of a) removal of tissue, aspiration of a cyst, or both at a biopsy site and b) marking the biopsy site with a clip, particularly in the context of a breast mammography procedure.

The present invention also provides additional benefits in the marking and/or treatment of a human tissue or otherwise by providing an encasement, adapted to be deployed with a marking clip, comprising agents used in the treatment of abnormal tissue and/or comprising a material suitably adapted for deployment with a clip. It should be appreciated that the encasement of the present invention may be used in any clip deployment device including any device disclosed or referred to herein, and those of the above-incorporated related applications.

DESCRIPTION OF THE INVENTION

Figure 1A:
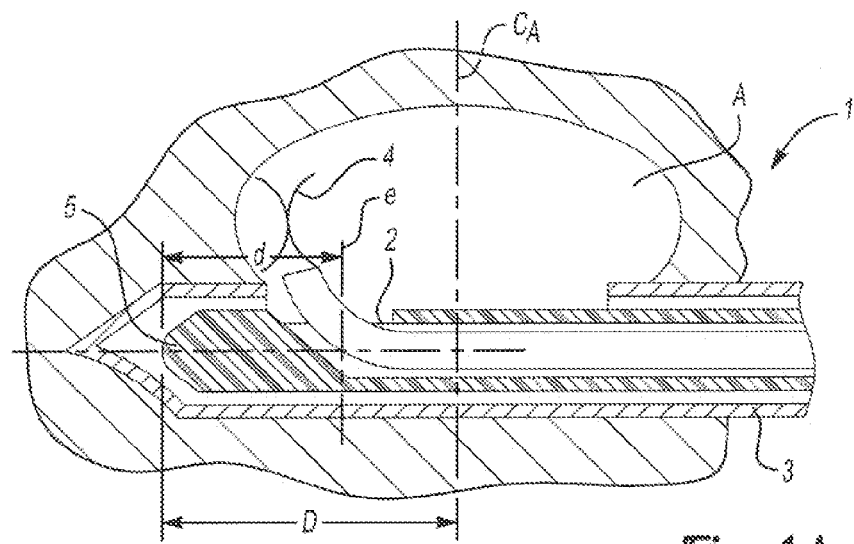
FIGS. 1a and b illustrate sectional views of a clip delivery device inserted into a cavity of a biopsy site.

The present invention provides improved devices and methods for the marking and treatment of tissue. Such applications may be particularly useful in conjunction with ultrasonic devices used for observing and/or monitoring specific tissue regions (e.g., breast tissue or otherwise). Such application may be advantageously used with tissue removal and aspiration devices configured for receiving a marking clip deployment device.

In one application, the present invention provides a clip delivery device and method for placement of a clip at a specified tissue region of interest. The device is configured for deployment of a clip at the specific region without undue manipulation of the device within the tissue. This is particularly useful in conjunction with an aspirating and/or tissue removal device, formed in part by a hollow needle, wherein the delivery device is placed within the needle and is configured for deployment of a clip through a side portion of the device and needle. The device is configured such that when the device is placed within the needle, the deployed clip will enter a central region of a specific tissue of interest with substantially no adjustment of the delivery device within the needle.

Accordingly, the traditional step of movement of the delivery device within a needle to insure proper deployment of the clip at a central region of a specific tissue of interest can be substantially eliminated. Furthermore, by deploying the clip to the central region, particularly in a central region of a cyst, the possible entanglement of the clip with the sidewalls forming the cyst is reduced. This is particularly useful when the marking clip is designed to engage tissue upon deployment and substantially limit migration of the clip through tissue. In view of the foregoing, the device simplifies deployment of a marking clip and insures proper securing and placement of the clip at a predetermined location, particularly a central region of the tissue of interest.

Still other benefits include greater flexibility and control of the deployment of a clip. The elimination of repositioning of the needle and/or the clip delivery device helps to remove guess work on where or when the clip should be deployed as the delivery device is manipulated. Also, this can eliminate the monitoring of any ultrasonic device in order to determine the position of the deployment device prior to deployment of the device. Accordingly, the delivery device provides a more accurate and reliable clip delivery device.

In another aspect, which may be used with the above deployment device or otherwise, the present invention provides a member used in conjunction with a marking clip to protect and/or improve deployment of the clip, provide medicinal benefits, treatments or otherwise. The member is configured to be deployed with the clip and preferably is attached or otherwise encloses at least a portion of the clip.

In one preferred configuration the member comprises an enclosure configured for encasing at least a portion of the clip, or is otherwise attached thereto, such that the encasement and clip are simultaneously deployed through any of the deployment devices described herein. In this configuration, the encasement may be configured for assisting in deployment of the clip. For example, the encasement may be configured to provide protection of the clip during deployment by acting as an intermediary to the clip and a push rod of the deployment device used for deploying the clip. Also, the clip may include an agent for assisting in the deployment of the clip or the agent may include one or more medicinal agents for treatment of the tissue surrounding the clip or otherwise.

In view of the foregoing, consistent with the teachings of U.S. application Ser. No. 10/631,204 and PCT/US2003/023995, the present invention provides a clip delivery device 10 that has a guide surface such as a ramp 140 on the inside of the delivery device, and the clip delivery device 10 is configured for placement within a hollow needle 12, preferably (though not necessarily required) having a side opening 14. The needle may be configured for aspiration, tissue removal, a combination thereof or otherwise, which may or may not be assisted by the side opening. One such delivery device includes a tubular member 16 having a hollow opening configured for receiving a pushrod 18 or other advancing mechanism. The device includes a side opening 20 located toward an end portion of the device for deployment of a clip 22. Accordingly, the side opening of the delivery device is configured to align with the side opening of the needle. Still further, upon insertion of the needle and the delivery device within tissue, the opening of the delivery device is coexisting with the center portion of a biopsy cavity, or otherwise, so that delivery of the clip requires little to no longitudinal adjustment of the device prior to deployment of the clip.

Figure 1B:
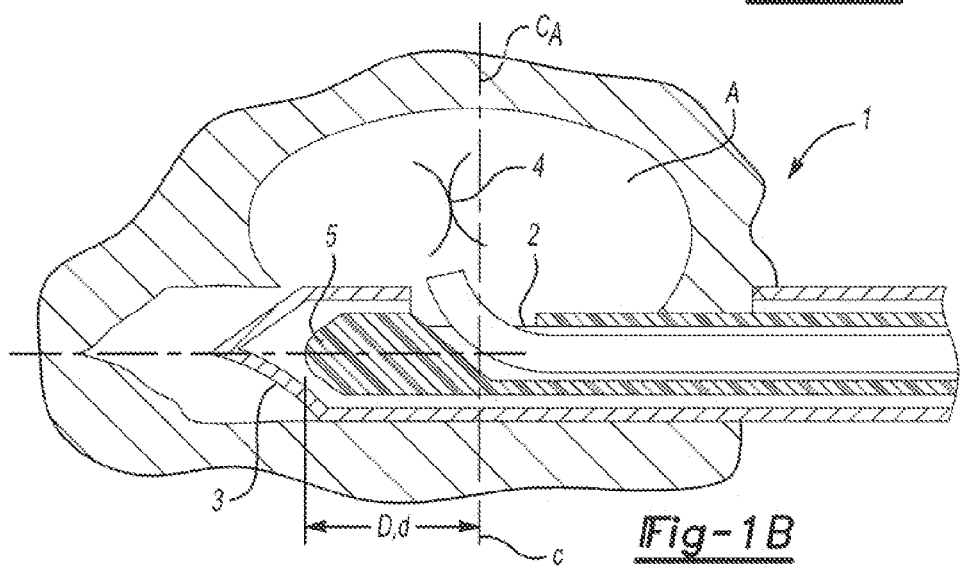
Figure 2:
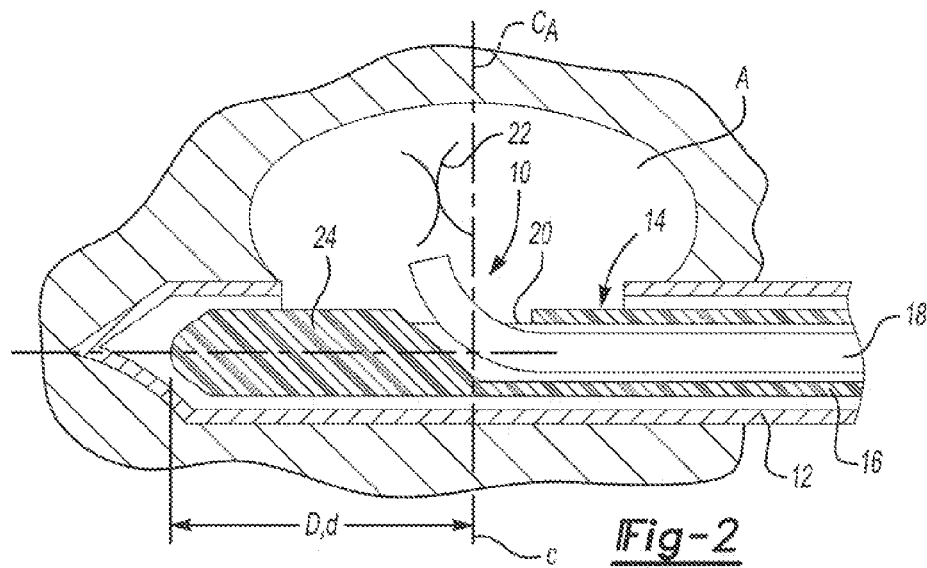
FIG. 2 illustrates a sectional view of a clip delivery device of the present invention inserted into a cavity of a biopsy site.

With reference to FIG. 2, the delivery device includes a leading portion 24 configured for aligning side opening of the delivery device with the side opening of the needle 12 and more preferably with a central portion of a biopsy site "$C_A$". As compared with conventional prior devices, the leading portion 24 of the present invention is longer than the leading portions shown in FIGS. 1A and 1B. Accordingly, it is not necessary to adjust the needle to deploy a clip in the central portion of a biopsy site. Furthermore, it would not be necessary to move the delivery device within the needle to position the device to deploy in the central portion of the biopsy site.

More particularly, relative to prior art devices, the present invention contemplates moving the side tube opening 20 of the clip deployment device 10 away from the leading portion so that the center "C" of the side opening will be approximately coexisting with a center portion "$C_A$" of the biopsy site "A". For example, the side tube opening may be located from the forward end of the leading portion at a distance of 5 mm, 10 mm, 15 mm, 20 mm, 25 mm or more. Similarly, the side tube opening may be located from the forward end of the leading portion at a distance of 5%, 10%, 15%, 20%, 25% or more of the length of the delivery device.

In one configuration, this includes moving the side tube opening proximally by about 5-15 mm and more preferably about 10 mm from the forward end of the leading portion 24. For example, as illustrated, the distance "d" between the forward end of the leading portion 24 and the center of the side hole is approximately the same as the distance "D" from the forward end of the leading portion to the center of the biopsy site. In reference to the configuration mention above, this would result in the distance "d" from the leading portion of the delivery device being about 8 to about 16 mm and even more preferably about 12 mm.

However, it should be appreciated that other configurations are available. For example, it is contemplated that multiple delivery devices may be provided having different distances "d" to correspond to the distance "D" to the center of the biopsy site "A". Accordingly, upon insertion of the needle proximate to the biopsy or cyst site, a deployment device may be selected base upon the size of the biopsy or cyst site. Therefore, with a larger biopsy site or cyst, a deployment device having a greater distance "d" will be selected for insuring deployment of the clip to a center portion of the site. It should be appreciated that the size of the cyst or biopsy site may be determined using common techniques in the field of art, include ultrasonic devices.

One preferred needle 12 that may be used with the delivery device includes any needle having a side opening at a first end and is suitable for receiving the clip delivery device 10 at a second end. Preferably, the gauge of the needle is about 8 to about 14 and more preferably about 11. As such, the gauge of the delivery device being inserted into the needle is about 9 to about 15 and more preferably about 12. It should be appreciated that the gauge of the delivery device is about 0.5 to about 1.5 smaller than the gauge of the needle.

In accordance with the present invention, there are further contemplated processes by which an instrument substantially as disclosed in FIG. 2 is provided for radiographic analysis, and particularly for mammography. The device is inserted into a breast and a biopsy performed at a biopsy site "A". Without a positive step of longitudinal re-positioning of the needle 12 or clip delivery device 10 of the instrument, such as by longitudinal movement in excess of about 3 mm, a clip 22 is delivered to the biopsy site "A".

Thus one method contemplates providing an instrument including a needle and a clip delivery device. The delivery device is inserted into the second end of the needle wherein upon insertion the side opening of the delivery device and the needle are generally aligned. As shown in FIG. 2, the needle and delivery device are inserted proximate to a biopsy site wherein the center of the side opening is located proximate to the center portion "$C_A$" of a biopsy site "A". The clip is thereafter delivered, via pushrod 18, along the hollow portion of the tubular member 16 in into the center portion "$C_A$" of a biopsy site "A" (e.g., so at least a portion of the clip overlaps with the biopsy site). The delivery of the clip within the biopsy site is essentially free of a step of longitudinal re-positioning by the user of the needle, clip delivery device, or both, and thus with a greater degree of accuracy of clip placement.

Alternatively, the needle alone may be inserted proximate to a site having a cyst or to be biopsied. With the needle inserted, on or more functions may be performed relating to the treatment or diagnosis of the tissue. Upon completion, the delivery device is inserted into the needle wherein the side opening of the delivery device and needle are generally aligned. A clip is then deployed as described above.

Upon deployment, the clip engages the surrounding tissue of the formed cyst or biopsy site to substantially prevent the clip from migrating to other portions of the cyst or otherwise. Accordingly, the clip substantially remains in the center portion "$C_A$" of a Biopsy site "A" or otherwise. Suitable clips that may be used comprise clips configured to engage tissue upon deployment. Particularly advantageous clip that may be used are clips configured to expand upon deployment to engage tissue. By example, suitable clips that may be used with the present invention can be found in commonly owned U.S. patent application Ser. No. 10/631,204, filed Jul. 31, 2003, herein incorporated by reference. Other suitable clips can be found herein as shown and described. Such clips generally include a first portion connected to a second portion at an apex, wherein at least one of the first, second or both portions are straight, arcuate or include a combination thereof. Such clips are generally configured to elastically deform to fit within a delivery device and subsequently return to an original shape upon exit.

In another aspect, the present invention further contemplates the use of an additional member with any of the clips 22 as described or referred to herein, in order to impart an additional function to the resulting implanted clip. Though the additional member typically will be attached to a clip, it might be separate from it but deployed during a single deployment operation (e.g., a single plunger stroke). However; preferably the additional member is in contact with the clip during deployment of the same. More preferably, the additional member is adapted to encase all or a portion of clip.

In one aspect, the additional member comprises an encasement 26 deployable with a clip. The term encasement may include any object, which includes or comprise agents adapted to assist in the treatment of tissue or any object that assist in the deployment of a marking clip. As such, it should be appreciated, though not limiting, that term encasement may include capsules, tablets or the like.

Figure 3:
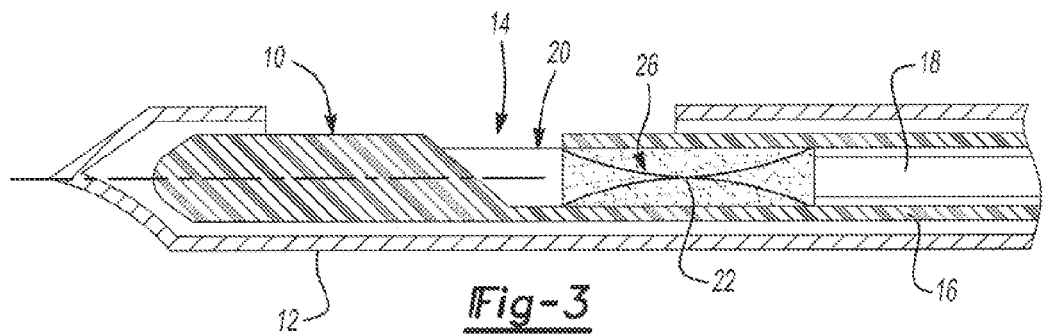
FIGS. 3 and 4 illustrates an encasement of the present invention in different stages of delivery through a clip delivery device.
Figure 4:
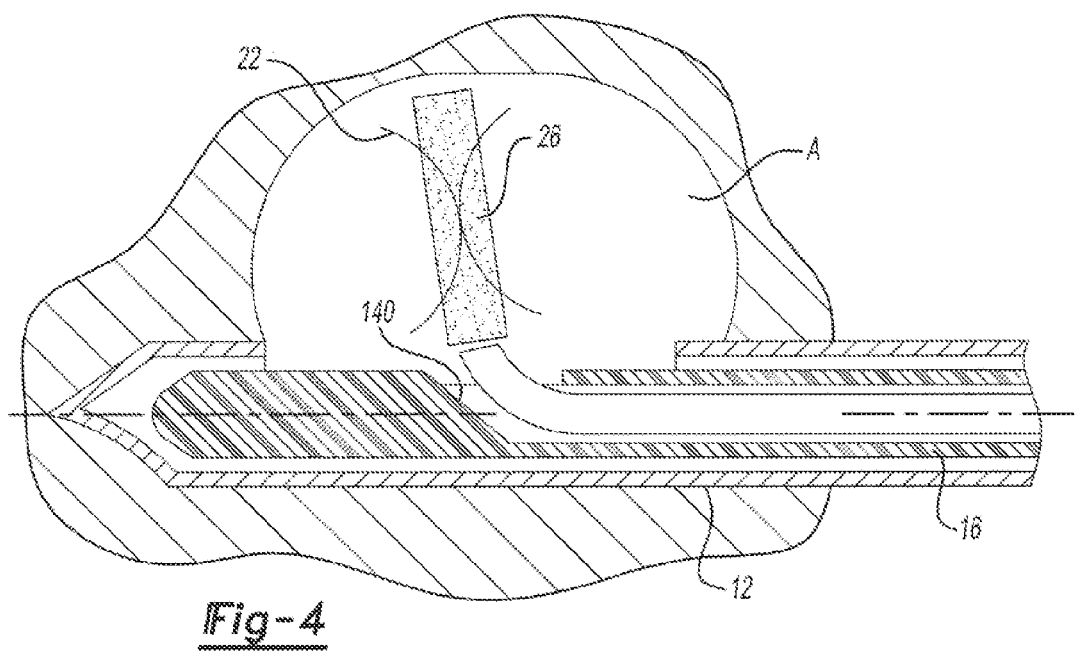
Figure 5:
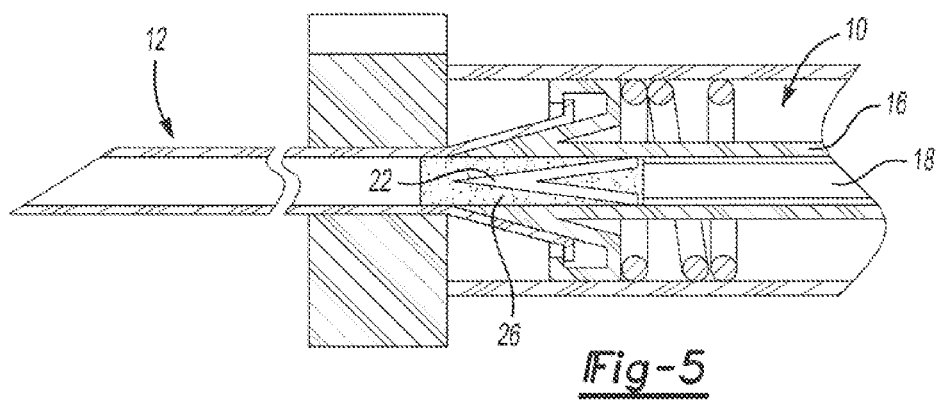
FIG. 5 illustrates another encasement of the present invention another clip delivery device.
Figure 6A:
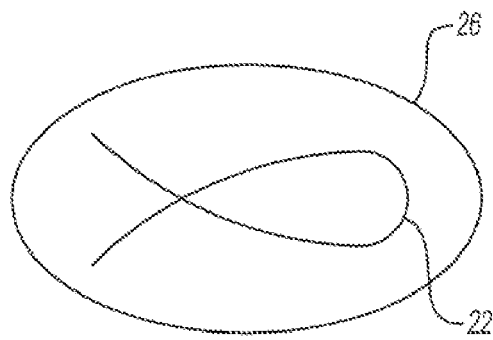
FIGS. 6a-e illustrates alternate encasement configurations of the present invention.
Figure 6B:
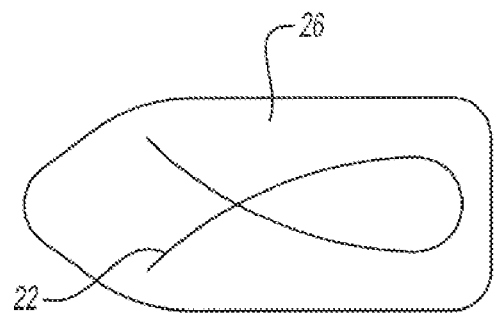
Figure 6C:
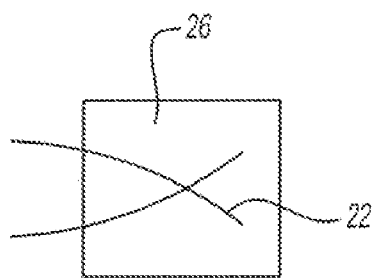
Figure 6D:
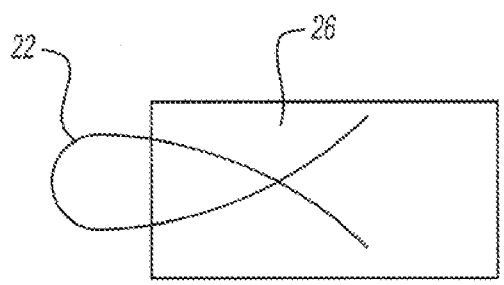
Figure 6E:
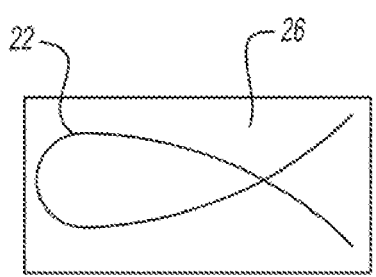

For example, as illustrated in FIGS. 3 and 5, the additional member may comprise an encasement 26 or other suitable structure adapted to protect the clip from forces encountered during deployment of the same. As such, when the clip 22 is longitudinally deployed along the delivery tube 16, the encasement absorbs or distributes the load applied by a drive member 18 over a broad region of the clip 22 so as to help prevent plastic or permanent deformation of the clip. The encasement may be adapted to prevent direct contact between the drive member and clip. Additionally, or alternatively, the encasement may further be adapted to completely encapsulate the clip so as to prevent contact of the clip with the surrounding interior walls of the delivery tube. Therefore, it is within the teachings of the present invention to at least, partially (if not completely) seal the clip within the encasement, either permanently or temporarily (e.g., with a biodegradable or bioerodible medium or the like, wherein expansion of the clip to a relaxed state occurs after an effective amount of encasement dissolves or otherwise degrades to allow the clip to expand therethough).

As demonstrated in FIGS. 1 a-B, 2 and 4, upon deployment the clip is configured to resist or restrict movement of the clip within the deployed region (e.g., cyst, biopsy site or otherwise). Therefore, one specific approach is to provide the encasement 26 so it does not prevent the clip 22 from expanding to its fully relaxed shape.

Alternatively, the encasement 26 may be designed to temporarily or permanently restrict the clip 22 from attaining its relaxed shaped, or limits the range of relaxation. For example, it is contemplated that the encasement comprises a material that is biodegradable or bioerodible, which diminishes in volume over time and thus reduces the availability of material that will constrain the clip when in an elastically deformed state. Alternatively, the encasement may comprise a time-release material adapted to diminish in volume, and optionally release one or more pharmaceutical agents or other agents over time. It should be appreciated that other processes of releasing an encapsulated agent are possible and within the scope of the present invention.

In yet another aspect, the encasement 26 may be deployed precisely to a biopsy site without a clip 22. It is possible that such encasement maintains its sized and/or shape over time, or it too might be capable of degrading, eroding or otherwise diminishing in volume.

The preferred dimensions of the encasement are such that any clip 22 located therewith fits at least partially, and in one example entirely within its volume. For example, referring particularly to FIGS. 3 and 5, optionally the length of the encasement 26 is greater than the length of the collapsed clip such that the end portions of the clip are protected. Also as previously discussed, the diameter of the encasement is such that the encasement can slidably move within the delivery tube 16 with a minimum amount of surface friction. As such, preferably, the encasement is cylindrical in shape (or otherwise has a complementary or otherwise compatible shape relative to the delivery tube shape) and has a diameter less than the inner diameter of the delivery tube. Suitable diameters of the encasement comprise a range of about between about ⅓ mm to about 2½ mm and more preferably about ⅔ mm to about 2 mm. The inside of the delivery tube also may be treated over at least a portion of its surface with a suitable low friction coating (e.g., a polyolefin, or fluorinated polymer, such as PTFE might line the tube).

However, it should be appreciated that alternatively the encasement 26 may be greater than the interior portion of the delivery tube 16. For example, the encasement may be sponge-like or otherwise compressible to fit within the delivery tube. As such, it is contemplated that the encasement may comprise a shape other than cylindrical and may or may not be symmetrical, geometrical or otherwise systematically configured member. Likewise, the encasement may comprise a plurality of components. Examples of various alternate configurations are shown in FIGS. 6a-e.

It is contemplated that the encasement 26 comprises a material suitable for use with marking and aspiration of tissue and comprises a material also suitable for use with a delivery device 10. It should be appreciated that the encasement may be rigid or flexible and may comprise an additional layer or otherwise use a material to reduce surface friction with the delivery tube during deployment. In one example, the material of the encasement comprises an elastic material so as to receive a portion of the clip 22 as it is compressed into the encasement and placed in the delivery tube 16. In another example, the material is pliable so as to allow the clip to expand from within the encasement to a location exterior to the encasement. In yet another example, the material is a biodegradable, bioerodible, another suitable time release material or otherwise configured to diminish in volume over time so as to release agents into the tissue, release the clip from within the encasement and attain its designed shape, a combination thereof or otherwise.

Suitable material that may be used to form the encasement includes plastics such as bio-compatible polymer, starches, salts, or the like. Other suitable materials include implantable metals such as stainless or surgical steel, a nickel containing metal, titanium or any other low corrosion biocompatible material. Still other suitable materials include non-ferromagnetic metal (such as titanium) that does not create artifact when imaging breast tissue, or the like, through magnetic resonance imaging (MRI).

The encasement 26 may include at least one first material in a matrix of a second material. It may include a single material or it may be a capsule that contains one or a plurality of items or phases of matter within its interior.

Optionally, as stated above, the encasement 26 may comprises one or more additional layers, materials, agents or otherwise to facilitate in the marking or treatment of a tissue. Examples, of additional materials are selected from lubricants, collagen, antibiotics, antiseptics, radiation seeds, chemotherapeutic agents, thrombosis activating agents, combinations thereof or otherwise.

Advantageously, the encasement, clips or otherwise comprises a material that is detectable using ultrasonic technology, radiography, tomography, magnetic resonance imaging, combinations thereof or the like. Examples of suitable encasements of the present invention includes pledgets, Gelfoam®, collagen, or the like.

In an alternative embodiment, it is contemplated that the encasement 26 may be used alone or with a clip to further assisting in the treatment of tissue. In one example the encasement may be utilized with a Radio Frequency Identification (RFID) device, or other element for location or proximity sensing, to assist in identification of previous medical treatment performed on a select tissue region. A RFID implant or other suitable electronic device, for example might be adapted to store information about a patient's medical history that can be retrieved subsequently. Thus a patient effectively becomes a walking medical file. In another example, the encasement may be used with cryoblation to assist in neutralizing portions of a tissue region through freezing or heating the tissue, with the use other associated equipment. In yet another example, the encasement 160 may be used chemotherapeutic agents that may be timed release or released via a remote controller or otherwise. In still another example, the encasement may comprise a chip or other sensing device for monitoring the growth of surrounding tissue and other matter, and optionally for providing an output signal or activating a medicinal release device in the event abnormalities are sensed. In still another example, the encasement may be used with brachytherapy, wherein the encasement releases radioactive seeds for the treatment of cancer. Combinations of any of the above uses are also contemplated.

It is contemplated that the clip 22 and the encasement 26 of the present invention comprises separate components or comprises a single component integrally formed.

It is further contemplated that other emerging technologies are within the scope of the present invention. For example, the present invention may further include cytologic or histologic technology, which provides a immediate testing (e.g., pathological testing) of a tissue sample while the delivery device, needle or both are still inserted into a tissue sample. As such, with the contemporaneous testing of a tissue sample, immediate measures can be taken to begin treatment of the tissue if found harmful. This is most advantageous when it is determined that the tissue is malignant or otherwise places the host in harm and the host is a non-surgical candidate.

For example, during excising of a tissue sample of a non-surgical candidate it is determined that the tissue is malignant or otherwise harmful, it is possible to insert an encasement, which may or may not have a clip, to begin treatment of the tissue as discussed herein.

It will be appreciated that the present invention employs a device substantially as disclosed in commonly invented and owned U.S. patent application Ser. No. 10/631,204 filed on Jul. 31, 2003 and U.S. Provisional Patent Application Ser. No. 60/547,844 filed on Feb. 26, 2004, hereby incorporated by reference, and various features and methods of use as advanced herein are inherent in the disclosure of the prior application. Any redundancy of disclosure herein is not an admission of a deficiency in such prior disclosure, but is provided in an abundance of caution and to help articulate benefits achievable with the subject technology.

Unless stated otherwise, dimensions and geometries of the various structures depicted herein are not intended to be restrictive of the invention, and other dimensions or geometries are possible. Plural structural components can be provided by a single integrated structure. Alternatively, a single integrated structure might be divided into separate plural components. In addition, while a feature of the present invention may have been described in the context of only one of the illustrated embodiments, such feature may be combined with one or more other features of other embodiments, for any given application. The use of different material combinations than those shown might also be appropriate, such as the substitution of metal for plastic, or plastic for metal. It will also be appreciated from the above that the fabrication of the unique structures herein and the operation thereof also constitute methods in accordance with the present invention.

The preferred embodiment of the present invention has been disclosed. A person of ordinary skill in the art would realize however, that certain modifications would come within the teachings of this invention. Therefore, the following claims should be studied to determine the true scope and content of the invention.

What is claimed is:

1. An improved device for marking a biopsy site, comprising:
   a needle having a side opening at a first end; and
   a clip delivery device comprising:
      a tube having a leading portion with a forward end and a side opening having a center, wherein the forward end of the leading portion of the tube is located at a distance of about 8 mm to 16 mm from the center of the side opening of the tube;
      a ramp guide surface in the tube;
      an elongated driver having an end portion located within the tube, the driver being adapted to slide within the tube to a position proximate to the side opening of the tube; and
      a clip that is at least partially encapsulated in an encasement and is located in the tube at a location that is axially forward of the elongated driver,
   wherein the needle is a piercing needle having a hollow portion configured for receiving the tube of the clip delivery device at a second end so that during deployment of the encapsulated clip to the biopsy site the needle houses at least a portion of the tube and at least a portion of the driver;
   wherein upon sliding the end portion of the elongated driver to a position proximate of the side openings of the needle and the tube, the clip is deployed precisely to a central portion of the biopsy site without the need to longitudinally re-position the needle and without having to longitudinally re-position the tube after a biopsy and prior to and/or during deployment.

2. The improved device of claim 1, wherein the tube has a gauge of about 9 to 15, and the encasement has a diameter of between about ⅓ mm to about 2½ mm.

3. The improved device of claim 2, wherein the encasement includes one or more additional layers, materials, or agents to facilitate in the marking or treatment of a tissue region.

4. The improved device of claim 3, wherein the encasement includes collagen.

5. The improved device of claim 2, wherein the encasement includes a thrombosis activating agent.

6. The improved device of claim 2, wherein the encasement is generally cylindrical and maintains its size, shape, or both over time.

7. The improved device of claim 2, wherein the encasement is bioerodible, biodegradable, or both.

8. The improved device of claim 1, wherein the elongated drive includes an end portion that is configured to extend up along the ramp.

9. An improved device for marking a biopsy site, comprising:
   a) an elongated delivery tube including:
      i. a longitudinal axis,
      ii. a leading portion with a forward end, and
      iii. an opening, having a center, in a sidewall of the elongated delivery tube axially spaced from the leading portion;
   b) an elongated push rod including a portion that slides within the elongated delivery tube and within the opening in the sidewall of the elongated delivery tube;
   c) a clip that is at least partially encased and is located in the elongated delivery tube and axially forward of the push rod;
   d) a ramp guide surface located in the tube, and inclined so that the ramp guide surface defines a rear end of the leading portion and of the opening in the sidewall of the elongated delivery tube,
   wherein upon sliding the elongated push rod to a position proximate of the side opening the clip is deployed precisely to a central portion of the biopsy site without the need to longitudinally re-position the tube after a biopsy and prior to and/or during deployment; and
   wherein the center of the opening in the sidewall of the elongated delivery tube is located about 8 mm to about 16 mm from the forward end of the leading portion.

10. The improved device of claim 9, further including a piercing needle with a side opening, wherein the improved device for marking the biopsy site is inserted at least partially into the piercing needle so that the clip can be inserted into the biopsy site.

11. The improved device of claim 9, wherein the ramp guide surface is a flat surface that in inclined and the ramp guide surface includes a bottom end of the ramp guide surface that begins on the inside of the tube and the ramp guide surface extends to a top end located at an edge of the opening in the side wall proximate to the forward end of the tube.

12. The improved device of claim 9, wherein the dip has a structure of generally two back to back C shaped segments while in a pre-deployment state and a post-deployment state.

13. The improved device of claim 12, wherein the encasement is between about ⅓ mm and about 2½ mm in diameter.

14. The improved device of claim 12 wherein the push rod extends into the opening in the sidewall of the elongated delivery tube so that the push rod pushes the clip up the ramp and into the biopsy site.

15. The improved device of claim 9, wherein the improved device is adapted for stereotactic deployment.

16. An improved device for marking a biopsy site, comprising:
   a) an elongated delivery tube including:
      a. a longitudinal axis,
      b. a leading portion with a forward end, and
      c. an opening, having a center, in a sidewall of the elongated delivery tube axially spaced from the leading portion;
   b) an elongated push rod including a portion that slides within the elongated delivery tube and within the opening in the sidewall of the elongated delivery tube;
   c) a ramp guide surface located in the tube; the ramp guide surface being inclined so that the ramp guide surface defines a rear end of the leading portion; and the ramp guide surface being located in the opening in the sidewall of the elongated delivery tube;
   d) a clip that is located in the elongated delivery tube and axially forward of the push rod,
   wherein upon sliding the push rod to a position proximate of the side opening the clip is deployed precisely to a central portion of the biopsy site without the need to longitudinally re-position the tube after a biopsy and prior to and during deployment;
   wherein the center of the opening in the sidewall of the elongated delivery tube is located about 8 mm to about 16 mm from the forward end of the leading portion, and
   wherein the clip includes an encasement that at least partially surrounds the clip so that the encasement protects the clip from forces encountered during deployment of the clip.

17. The improved device of claim 16, further including a piercing needle with a side opening, wherein the elongated delivery tube is inserted into the needle so that the clip can be inserted into the biopsy site.

18. The improved device of claim 17, wherein the leading portion is configured so that the clip when deployed will enter a central region of a specific tissue of interest with substantially no adjustment of the elongated delivery tube within the piercing needle.

19. The improved device of claim 16, wherein the push rod is configured so that during deployment the end of the rod extends to the end of the tube and through the opening in the sidewall of the elongated delivery tube.

20. The improved device of claim 16, wherein the clip extends along an axis between a first end and a second end, and the clip comprises a metal structure consisting essentially of:
   a first arc segment having a first end located at the first end of the clip and a second end located at the second end of the clip;
   a second arc segment having a first end located at the first end of the clip and a second end located at the second end of the clip, the second arc segment being coplanar with the first arc segment;
   an encasement includes or comprises agents adapted to assist in the treatment of tissue; and
      an apex disposed along the clip axis defining where the first and second arc segments adjoin and converge,
      wherein, after being driven through the opening in the sidewall of the elongated delivery tube, the metal structure is configured to engage breast tissue, and the metal structure is configured so that
   (i) it resides entirely within the elongated delivery tube prior to being driven through the opening in the sidewall of the elongated delivery tube,
   (ii) it deploys through the opening in the sidewall of the elongated delivery tube, and
   (iii) in both an original pre-deployment state and a post-deployment state:
   the first ends of the first and second arc segments project in a direction outward relative to the clip axis, and the second ends of the first and second arc segments project in a direction outward relative to the clip axis, and
   the first ends of the first and second arc segments project in a direction generally away from the second ends of the first and second arc segments;
   while it resides within the elongated delivery tube, prior to being driven through the opening in the sidewall of the elongated delivery tube, and after being driven though the opening in the sidewall of the elongated delivery tube the first and second arc segments are arcuate; and
   wherein the first ends and the second ends of the first and second arc segments engage breast tissue after being driven the opening in the sidewall of the elongated delivery tube, and thereby substantially prevent migration of the deployed clip within the breast.

* * * * *